(12) United States Patent
Paasimaa et al.

(10) Patent No.: US 6,398,814 B1
(45) Date of Patent: Jun. 4, 2002

(54) BIOABSORBABLE TWO-DIMENSIONAL MULTI-LAYER COMPOSITE DEVICE AND A METHOD OF MANUFACTURING SAME

(75) Inventors: Senja Paasimaa, Helsinki; Minna Kellomäki; Pertti Törmälä, both of Tampere, all of (FI)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/152,554

(22) Filed: Sep. 14, 1998

(51) Int. Cl.⁷ .................................................. A61F 2/36
(52) U.S. Cl. ................... 623/23.51; 623/23.52
(58) Field of Search ................ 623/16, 13.18, 623/1.27, 1.44, 1.45, 1.46, 1.47, 1.48, 1.49–1.54, 23.51, 23.53, 23.54, 23.52, 23.58, 23.59, 23.6; 606/194; 428/131, 36.92; 424/426

(56) References Cited

U.S. PATENT DOCUMENTS

| | | | |
|---|---|---|---|
| 4,400,833 A | | 8/1983 | Kurland |
| 4,898,186 A | | 2/1990 | Ikada et al. |
| 4,968,317 A | | 11/1990 | Törmälä et al. |
| 5,084,051 A | | 1/1992 | Törmälä et al. |
| 5,455,100 A | * | 10/1995 | White ............... 428/131 |
| 5,593,425 A | * | 1/1997 | Bonutti et al. ........ 606/232 |
| 5,904,967 A | * | 5/1999 | Ezaki et al. ........ 428/36.92 |
| 5,916,585 A | * | 6/1999 | Cook et al. .......... 424/426 |
| 6,187,039 B1 | * | 2/2001 | Hiles et al. .......... 623/1.44 |

FOREIGN PATENT DOCUMENTS

| | | |
|---|---|---|
| EP | 0274898 | 7/1988 |
| GB | 2085461 | 4/1982 |
| WO | WO 90/04982 | 5/1990 |
| WO | WO 90/12605 | 11/1990 |
| WO | WO94/15588 | 7/1994 |
| WO | WO 96/00592 | 1/1996 |
| WO | WO96/41596 | 12/1996 |
| WO | WO98/14134 | 4/1998 |
| WO | WO 98/30252 | 7/1998 |

OTHER PUBLICATIONS

R.M. Pilliar, Powder Metal–Made Orthopedic Implants with Porous Surface for Fixation by Tissue Ingrowth, Clinical Orthopaedics and Related Research, vol. I 176, 1983, pp. 42–51.

S. Vainiopaa, et al, Surgical Applications of Biodegradable Polymers in Human Tissues, Progress in Polymer Science, vol. 14, 1989, pp. 679–716.

J. Eitenmüller, et al., An In Vivo Evaluation of a New High Molecular Wt. Polylactide Osteosynthesis Device, European Congress on Biomaterials, Bologna Italy, Sep. 14–17, 1986, p. 94.

Törmälä, Biodegradable Self–Reinforced Composite Materials; Manufacturing Structure & Mechanical Properties, Clinical Materials, vol. 10, 1992, pp. 29–34.

O.H. Andersson, et al., Bioactive Glass, Biomaterials Today and Tomorrow, Proceedings of the Finnish Dental Society Days of Research, Tampere, Finland, Nov. 10–11, 1995, pp. 15–16.

J.C. Behiri, et al., Advanced Bone Cement For Long Term Orthopaedic Applications, Bioceramics, vol. 4 Edited by W. Bonfield, et al., Proceedings of the 4th International Symposium on Ceramics in Medicine, London, UK, Sep. 1991, Butterworth—Heinemann Ltd., Oxford, 1991, pp. 301–307.

(List continued on next page.)

*Primary Examiner*—Corrine McDermott
*Assistant Examiner*—Hieu Phan
(74) *Attorney, Agent, or Firm*—Kenyon & Kenyon

(57) ABSTRACT

This invention relates to bioabsorbable multi-layer two-dimensional composite devices and their method of manufacture by spot welding the layers of the device at designated points, which devices can easily be cut into any desirable form by a surgeon during operation on a patient.

10 Claims, 2 Drawing Sheets

Side View

Top View

OTHER PUBLICATIONS

W. Bonfield, et al., In Vivo Evaluation of Hydroxyapatite Reinforced Polyethylene Composites, Biological & Biomechanical Performance of Biomaterials, Edited by P. Christel, et al., Elsevier Science Publishers, 1986, pp. 153–158.

C. Doyle, et al., In Vitro & In Vivo Evaluation of Polyhydroxybutyrate and of Polyhydroxybutyrate Reinforced with Hydroxyapatite, Biomaterials, vol. 12, 1991, pp. 841–847.

Chase S. W., Herndon C.H., "The fate of autogenous and homogenous bone grafts: A historical review," *Journal of Bone Joint Surgery* 37 A, 1955, pp. 809–841.

Prolo D.J., "Cranial defects and cranioplasty, in Wilkins RH, Rengachary SS (eds): Neurosurgery," New York, McGraw–Hill, 1984, pp. 1647–1656.

Grant F.C., Norcross N.C., "Repair of Cranial Defects By Cranioplasty," *Annual Surgery* vol. 110, 1939, pp. 488–512.

Reeves D.L., "Cranioplasty," Springfield, IL, Charles C. Thomas, 1950, pp. 3–119.

Wolff J.I., Walker A.E., "Cranioplasty, Collectective review," *International Abstracts Surgery* 81, 1945, pp. 1–23.

Habal M.B., Leake D.L., Maniscako J.E., "A new method for reconstruction of major defects in the cranial vault," *Surgery Neurology* 6, 1976, pp. 137–138.

Karvounis P.C., Chiu J., Sabin H., "The use of prefabricated polyethylene plate for cranioplasty," *Journal of Trauma* 10, 1970, pp. 249–254.

Black S.P.W., "Reconstruction of the supraorbital ridge using aluminum," *Surgery Neurology* 9, 1978, pp. 121–128.

Heller J., Poloy(ortho esters), Advances in Polymer Science 107:41–92, 1993.

Peter D. Costantino, et al. "Synthetic biomaterials in Facial Plastic and reconstructive Surgery." *Facial Plastic Surgery* vol. 9, No. 1. Jan. 1993, pp. 1–15.

P. Törmälä et al., "Bioabsorbable polymers: materials technology and surgical applications," Proc. Instn. Mech. Engrs., vol. 212, Part H., pp. 101–111.

S. Paasimaa et al., Development of a Bioabsorbable Finger Joint Prosthesis: Material Selection, $13^{th}$ European Conf. On Biomaterials, Sep. 407, 1977, pp. 146.

Rogers et al., "Absorbable Mesh Splenorrhaphy for Severe Splenic Injuries: Functional Studies in an Animal Model and an Additional Patient Series," The Journal of Trauma, vol. 31, No. 2, 1991, pp. 200–204.

Nagy et al., "Experience with Three Prosthetic Materials in Temporary Abdominal Wall Closure," The American Surgeon, vol. 2, May, 1996, pp. 331–335.

Rahman, et al., "Silicone Granulomatous Reactions After First Metatarsophalangeal Hemiarthroplasty," British Editorial Society of Bone and Joint Surgery, vol. 75–B, No. 4, Jul. 1993, pp. 637–639.

Kossovsky et al., "An Unusual Case of Biomaterials Pathology Discovered at Autopsy Using X–Ray Energy Spectroscopic Techniques," Biomaterials Bioreactivity Characterization Laboratory and Division of Anatomic Pathology, Apr. 7, 1989, pp. 148–152.

Ashammakhi et al., "Strength retention of self–reinforced polyglycolide membrane: an experimental study," Biomaterials 1995, vol. 16, No. 2, pp. 135–138.

Pizzoferrato et al, "Biomaterials and Clinical Applications," Proceedings of the Sixth European Conference on Biomaterials, Bologna, Italy, Sep. 14–17, 1986; 759–764.

McDowell et al., "The McDowell Series of Plastic Surgical Indexes," vol. 1, The Zeis Index and History of Plastic Surgery 900 B.C.—1863 A.D., pp. 51–52.

* cited by examiner

Side View  Top View

Side View  Top View

BIOABSORBABLE TWO-DIMENSIONAL MULTI-LAYER COMPOSITE DEVICE AND A METHOD OF MANUFACTURING SAME

BACKGROUND OF THE INVENTION

The present invention relates to bioabsorbable two-dimensional (2-D) multi-layer composite medical devices and to a method for manufacturing them by spot welding the layers together. The 2-D composites of the present invention can be easily cut into any desirable form by a surgeon during an operation on a patient.

2-D fabric implants are widely used in different medical operations. Both rigid and flexible implants are needed and used in the art. The required properties of such devices vary depending on the application and implantation site. Such applications can be found, for example, in bone fracture, bone augmentation and in other fixation applications, as well as guided tissue regeneration and in soft tissue closure.

However, meshes made of polyglycolic acid and of copolymers of glycolic acid and lactic acid, like DEXON (available from Davis & Geck, USA) and VICRYL (available from Ethicon GmBH, Hamburg Germany) meshes, lose their strength much too fast for many types of surgical applications. Indications of such disadvantageous early degradation include, for example, the development of a disabling gigantic hernia when DEXON mesh is used in an abdominal wall closure. See Nagy K. K., Fildes J. J., Mahr C., Roberts R. R., Krosner S. M., Joseph K. T., Barrett J., Experience with Three Prosthetic Materials in Temporary Abdominal Wall Closure. The American Surgeon, vol. 62, May 1996, pp. 331–335, the entire disclosure of which is incorporated herein by way of this reference. On the other hand, rapidly degrading 2-D fabric devices also have advantages over more slowly degrading or biostable 2-D fabric devices, which advantages include active induction of scar formation. See Rogers F. B., Baumgartner N. E., Robin A. P., Barrett J. A., Absorbable Mesh Splenorrhaphy for Severe Splenic Injuries: Functional Studies In An Animal Model and an Additional Patient Series, Journal of Trauma 31 (2) 1991, pp. 200–204; and Ashammakhi N., Mäkelä E. A., Vihtonen K., Rokkanen P., Kuisma H., Törmälä P., Strength Retention of Self-reinforced Polyglycolide Membrane: An Experimental Study. Biomaterials 16 (2) 1995, pp. 135–138, the entire disclosures of each of which are incorporated herein by way of this reference.

Also, many biostable (nonresorbable) polymers, polymer blends and elastomers are used as raw materials in manufacturing flexible 2-D fabric implants. However, the use of such materials can cause problems for the patient on a long term basis. One such problem is that loose debris may be released from the implant due to wear, fatigue and/or wearing away of the surrounding tissue environment, which debris may cause chronic inflammation reactions in the patient. See Kossovsky et al., Giant Cell Myocarditis Associated with Silicone, Am J Clin Pathol (1999) 93:148–152; and Rahman et al., Silicone Granulomatous Reactions After First Metarasophalangeal Hemiarthroplasty, Journal of Bone Joint Surgery (1993), 75-B:637–9, the entire disclosures of each of which are incorporated herein by way of this reference. These kinds of implants can also be too stiff and abrasive for tissue and, therefore, result in an unacceptably high rate of fistula formation. See Nagy et al., supra.

BRIEF SUMMARY OF THE INVENTION

The present invention relates to either rigid or flexible bioabsorbable 2-D composite implants and their manufacturing method. These composites can easily be cut into desirable forms by a surgeon during an operation. The composite implant of the invention includes at least two functional layers combined together by a spot welding method, using, e.g., a welding tool whose welding surface contains three-dimensional spots (i.e., points or protuberances emerging from the welding surface). Such welding, performed as described in this patent application, provides the implant of the invention with structural advantages over the prior art sewed implants (which have layers that are attached together by sewing as, e.g., described in U.S. Pat. No. 4,400,833, the entire disclosure of which is incorporated herein by way of this reference). For example, because of the way it is made, the implant of the invention has a surface that is intact and contains no pin holes, through which, for example, body fluids could flow or cells could grow or migrate.

Additional advantages are imparted to the implant of the invention when at least one resorbable film (continuous sheet) component is included in the structure of the implant. In that case, tissue growth through the implant is prevented by the film and, therefore, such devices can be used in applications where separation of two different tissue types for a period of time is essential during the tissue healing period.

The spot welding method of this invention serves to only partially attach together the multiple layers of the laminate composite, at the various points of the spot welding. This partially attached structure provides advantages over the structure of laminate composite implants made from various layers that are completely fixed and compressed onto one another, thereby forming a coherent laminated piece of composite material (e.g., by pressing the layers completely together using heat and pressure). In such completely fixed composites, layered implants, either one or all layers can be severely damaged due to the heat and/or pressure applied to make the implant. For example, the polymeric fibril structures in the layers can lose the initial strength needed for effective function after implantation.

The above disadvantages are overcome by the implant of the present invention, due to its manufacture by spot welding. With the spot welding process of the invention, the fibrillated polymer structures (for example, a mesh) used in making the composite implant of the invention are only partially exposed to heat and pressure at the points of the welding and, therefore, any damage to the implant is localized at those points (spots) of welding. Also, since the laminate layers of the implant of the invention are attached by spot welding, the structure remains more flexible than the prior art compressed, completely fixed, layered implants.

The pattern which the welding tool leaves on the implant can comprise, e.g., groups of lines or welding spots, depending on the configuration and spacing of the welding spots (points) on the welding surface of the tool. Such spots can be either round, oval or angular shaped, or a combination of spot geometries and spacings can be applied. Welding can be performed by applying energy and/or pressure to the welding spots on the welding surface and applying the welding tool to the layers of the composite or by subjecting those layers of the composite to ultrasound, using an ultrasonic welding apparatus with appropriately shaped tool. By varying the materials used and the shape and configuration of the welding tool surface, the properties of the devices can be customized in a wide range.

DETAILED DESCRIPTION OF THE INVENTION

Figure 1:
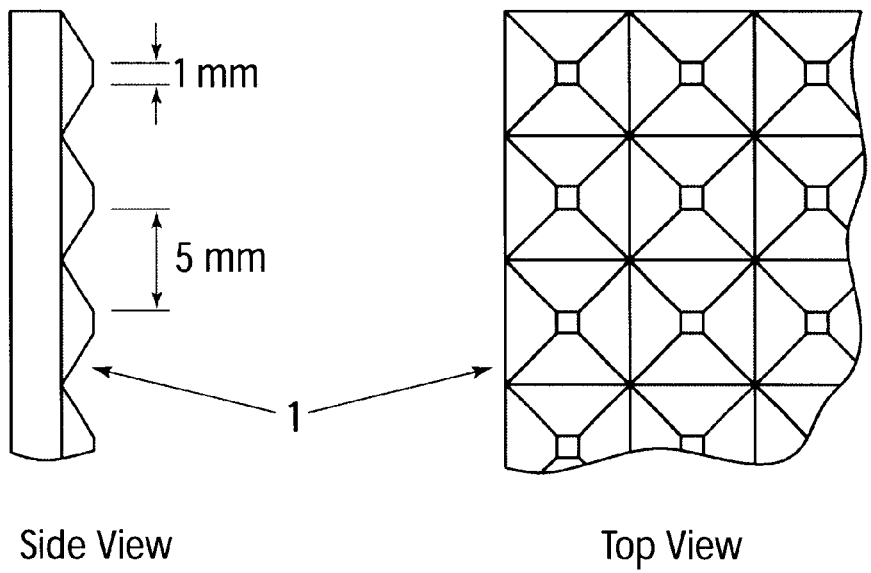
FIG. 1 shows schematically in two views (a side view and a top view) the geometry of the surface of a welding tool suitable for making the implants of the invention, as in Example 1 herein, the welding tool having diamond shaped welding spots 1 having a dimension of 1×1 mm and a distance between adjacent diamond shaped spots of 5 mm (FIG. 1 is not, however, drawn to scale in regard to the size of the spots and distance between the spots).

The present invention relates to a method of manufacturing implantable two-dimensional bioabsorbable multi-layer composite implants, which composite implants are flexible, but strong, and which can easily be cut into desirable forms by a surgeon during an operation.

In this invention, it has been found that the properties of a 2-D implant can be modified across a wide range, by manufacturing a multi-layer composite using a spot welding method. In the spot welding method of the invention, the implant is made by combining at least two functional layers and partially attaching them to one another by spot welding. The surface of the welding tool used to make the implants of the invention is shaped in such a way as to leave welding lines or spots on the implant after welding, due to the spots (points) on that surface. One skilled in the art can select a tip configuration for the welding tool of various dimensions and containing various different figures and/or different intermediate spacings between welding spots, depending on the desired welded structure for the implant. The form of the welding tool surface can be round, oval and/or angular and contain a combination of different spots, forms or lines at the welding surface.

On completion of the implant, the proportion of the welded area of the implant to the total area of the implant should be less than 50 percent, most preferably between 1 and 40 percent, to obtain the desired composite laminate. In the method of the invention, (1) a film and a fabric, or (2) a film and another film or (3) a fabric and another fabric, or (4) more than two different film and/or fabric layers can be combined to yield a laminate implant that retains the fibrous structure of any fabric or fabrics used in making the implant, in order to allow tissue growth into the fabric structure of the implant. Likewise, the intactness of the film component (or film components) is retained in the completed implants prepared under the method of the invention.

In the case where the laminate structure of the invention has at least one film layer (solid or continuous layer), the implant therefore has a sealing and/or tissue separating function. However, if only porous structures are used (no films) to make the implant, tissue can grow through the implant and practically no tissue-separating function exists in the implant. By changing materials, structures of the layers, or the size, shape, dimensions and density or spacing of welding spots or lines, implants having structures from hard and rigid to soft and flexible can be prepared according to the invention.

Welding can be performed by imparting energy, like heat and/or to pressure, to the lines or spots (figures or points, e.g., diamond shapes) on the welding surface of the welding tool and applying that welding surface on the layers (components) to be combined to form the implant of the invention. Suitable welding tools for making the implants of the invention are, for example, a heated compression molding plate or a surface-modified calender. The welding temperature used to weld the implants of the invention is advantageously near the softening point of any one of the materials in the implant having the lowest softening temperature.

Implants of the invention can also be prepared by ultrasound, using an ultrasonic welding apparatus. In that case, the welding time and pressure should be optimized to suit the properties of all components (layers) used to make the implant, especially the most sensitive components. For example, if too much energy (e.g., pressure) is applied to the layers of the implant or if the layers are exposed to that energy for too great a time period, then those layers may be damaged during the ultrasonic welding process. Such damage is avoided by selecting welding time periods and pressures in accordance with the properties (e.g., melting point) of the materials used in making the implant.

In implants of the prior art made by the complete heating and/or compressing of either one or all of the layered laminate components, the structure of the laminate implant can be severely damaged due to that heat and/or pressure. In particular, the polymeric fibril structures of the implant can completely lose their initial strength. This is not the case when spot welding is applied, as in the present invention, because the fibrillated polymer structure (for example, in a mesh) is only partially exposed to heat and pressure at the points of welding, and, therefore, damage, if any, is localized at the points of welding. Also, when layers are combined that have melting temperatures or temperature ranges that are close to each other, by spot welding the structure remains more flexible than when those components are completely joined together by heat and/or pressure, as in the prior art devices.

The 2-D composite devices manufactured according to this invention can be produced of bioabsorbable fabrics, non-wovens, knitted fabrics, fleeces, felts or films (either stiff or flexible bioabsorbable films), produced, e.g., with methods well known in the art of plastics and textile technologies. See, e.g., Paasimaa et al. WO 98/14134, the entire disclosure of which is incorporated herein by way of this reference.

The laminate layers used in this invention can have pores or they can be dense. At least one layer (component) of the implant may have an open, porous structure, which is at least partially retained even after the welding procedure. The pore size of at least one of those layers should be between 30 $\mu$m and 1500 $\mu$m, preferably between 50 $\mu$m and 1000 $\mu$m, to enable the tissue ingrowth into the device. Other layers of the implant can be either porous, in order to enable the tissue ingrowth or on growth, or they can be solid (e.g., films) to prevent tissue fluid flow or tissue growth through the device, depending on the application.

Each of the layers (including fabrics and films) of the 2-D composite devices manufactured according to this invention can be made of a bioabsorbable polymer, copolymer, polymer blend, polymer composite or by combining different polymer components. In medical, technical and patent literature there have been presented many bioabsorbable polymers that can be used as a raw material for the composite layers manufactured according the method of this invention. There are, for example, suitable bioabsorbable aliphatic polyesters, polyanhydrides, poly (ortho esters), etc. polymers for use in making the layers of the invention, which materials are described in many publications, such as Törmälä et al., Bioactive and Biodegradable Composites of Polymers and Ceramics or Glasses and Method to Manufacture Such Composites, U.S. patent application Ser. No. 08/921,533, filed on Sep. 2, 1997; and Törmälä et al., Bioabsorbable Polymers: Materials Technology and Surgical Applications. Proceedings of the Institution of Mechanical Engineers, Journal of Engineering in Medicine, vol. 212, no H2 (1998), pp. 101–111, the entire disclosures of each of which are incorporated herein by way of this reference. In addition, different bioabsorbable ceramics, ceramic-glasses and bioactive glasses can be used as fillers, as reinforcing components or as biologically functional components in the form of particles, flakes, fibers, films and/or fabrics, etc. in the invention. Examples of such materials are presented also in U.S. patent application Ser. No. 08/921,533. Using such materials, after implanting the bioabsorbable implant of the invention in a patient, the device will eventually disappear totally from the body and will not cause any chronic inflammations due to the permanent presence of loose debris from fractionating biostable materials.

The thickness of each separate layer of the implant can vary typically between 10 $\mu$m and 2000 $\mu$m, most preferably between 50 $\mu$m and 1000 $\mu$m. The total thickness of the implant is determined by the thicknesses of separate layers of the composite. The implant (device) itself can be round, rectangular, triangular or of any other desirable shape. Its dimensions depend on the size of the defect or wound to be covered.

Different drugs and/or growth factors, cultured cells and proteins can easily be added into the structure of the composite implant. Because only the localized welding sites are heated, sensitive agents in the laminate structure between the welding spots are not destroyed by thermal degradation or coagulation. When ultrasonic welding is used to make the implants of the invention, sensitive therapeutic agents can remain active even at the points of welding. See WO 94/15588, the entire disclosure of which is incorporated herein by way of this reference. Drugs and/or growth factors also can easily be added into the composite implant during the operation by a surgeon if, e.g., the agents are sensitive to the sterilization method used on the composite implant. Such therapeutic agents can then be in the form of a paste, mixed into a liquid (for example, physiological saline solution) or as powder.

The further function of this invention is described in the following, non-restrictive examples.

EXAMPLE 1

A three-layer, 2-D composite device for arthroscopic abdominal wall defect closure was made from (1) commercial polyglycolide (PGA) bioabsorbable DEXON MESH (available from Davis&Geck, USA), (2) a film made of copolymer of $\epsilon$-caprolactone and L-lactic acid, P($\epsilon$-CL/L-LA), having monomer ratio of 80/20 ($M_W$=210 000, made at and available from Helsinki University of Technology, Finland) and (3) a of P(L/D)LA fiber fabric made of multifilament fibers melt-spun of copolymer of L- and D-lactic acid having respective monomer ratios of 96/4 (i.v. (inherent viscosity)=6.8 dl/g, available from Purac biochem b.v., Netherlands). In such a composite device the function of the polyglycolide mesh is to induce fibrogenesis and scar tissue formation. The flexible P($\epsilon$-CL/L-LA) film prevents PGA debris release into the abdominal cavity, where it could cause tissue-to-tissue adhesions, while still keeping the implant very flexible. The P(L/D)LA fabric acts as a long term reinforcing component for the composite implant.

The P($\epsilon$-CL/L-LA) film of thickness 80 $\mu$m was prepared by a single screw extruder (available from Axon, Sweden) and by biaxial orientation at elevated temperature (55°–90° C.). The zone temperatures in the extruder barrel were between 60°–180° C.

The fibers were melt-spun with the single screw extruder (Axon, Sweden), where the polymer melt (at temperatures ranging from 200°–270° C.) was pressed through four round die holes having diameter of 0.4 mm. After cooling, filaments were oriented freely in a two-step process at elevated temperature (60°–140° C.) to a draw ratio of 4 to 8. The final filament diameter was 50 $\mu$m. The filaments were knitted by using a weft-knitting machine, with the fabric having loop size ca. 1 mm.

The layers (1), (2) and (3), above, were combined together by using the spot welding method according to this invention. The surface of the tool plate had diamond shaped welding spots. The size of the welding spots was 1×1 mm and the distance between adjacent spots was 5 mm. FIG. 1 shows schematically the geometry of the welding tool surface. The layers (1)–(3) were combined between the tool plate and the smooth plate by compression molding, using a compressive pressure between 2–20 MPa, and the temperature of the tool plate was kept between 60°–120° C. The final composite had a spot welded, flexible structure and thickness of 0.6 mm. The composite implant itself measured 100 mm×150 mm and was sterilized with γ-irradiation.

EXAMPLE 2

A 2-D composite device, to cover filled bone defects, was made of an extruded film with thickness of 0.5 mm made of a copolymer of L-lactic acid and D,L-lactic acid, P(L/DL) LA, having a respective monomer ratio of 70/30 (with inherent viscosity 6,1 dl/g, available from Boehringer Ingelheim, Germany) and of a woven bioactive glass fabric with the fiber thickness of 20 $\mu$m, chemical composition of $Na_2O$ 6 wt-%, $K_2O$ 12 wt-%, MgO 5 wt-%, CaO 20 wt-%, $P_2O_5$ 4 wt-% and $SiO_2$ 53 wt-%, and approximate porosity of 100 $\mu$m (made at and available from the Institute of Biomaterials, Tampere University of Technology, Finland). The function of the bioactive glass fabric is to enhance new bone formation into the defect. The purpose of the P(L/DL) LA film is to act as a long term reinforcing component for the composite implant.

Figure 2:
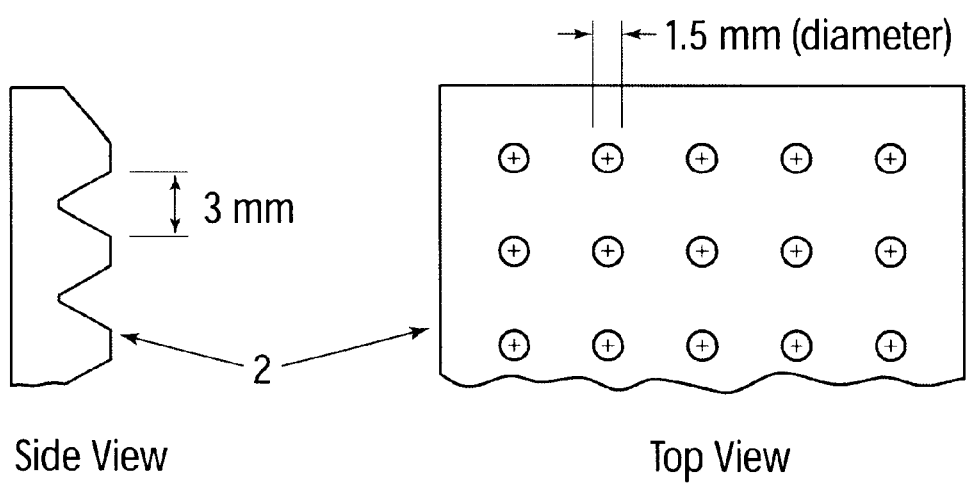
FIG. 2 shows schematically in two views (a side view and a top view) the geometry of the surface of a welding tool suitable for making the implants of the invention, as in Example 2 herein, the welding tool having round shaped welding spots 2 having a 1.5 mm diameter and a distance between adjacent diamond shaped spots of 3 mm (FIG. 2 is not, however, drawn to scale in regard to the size of the spots and distance between the spots).
Figure 3A:
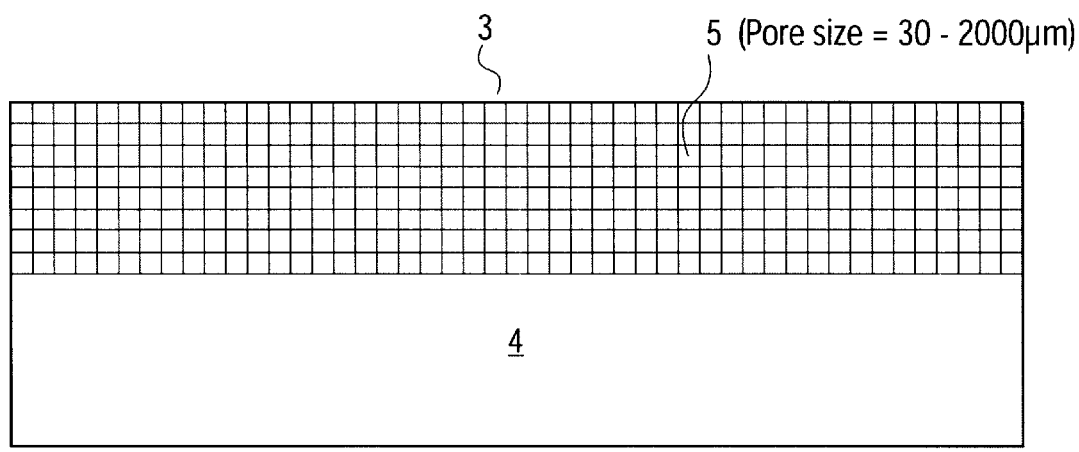
FIG. 3A shows, schematically, the preparation of an embodiment of the invention, prior to spot welding, having a first porous layer 3 and a second continuous film layer 4, wherein the pore size of the porous layer may be from 30 to 2000 $\mu$m.
Figure 3B:
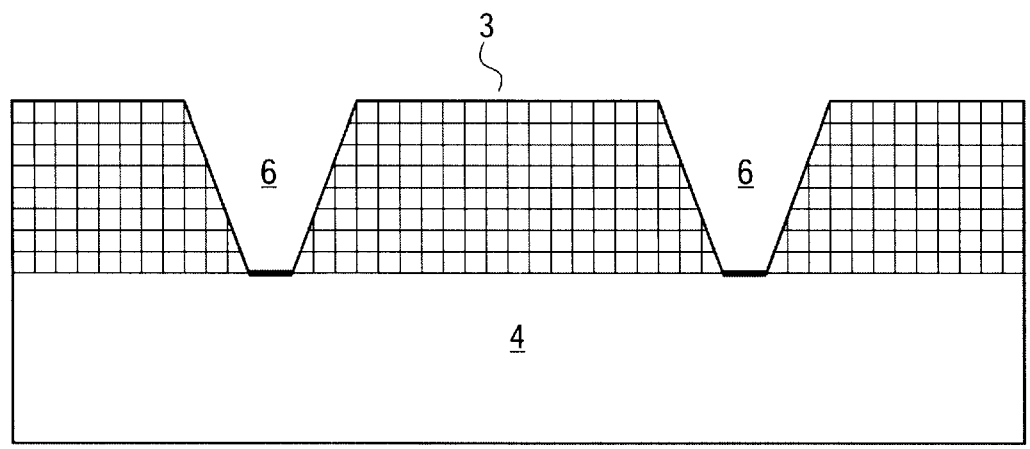
FIG. 3B shows, schematically, an embodiment of the invention after a spotwelding tool like that depicted in FIGS. 1 and 2 has been applied to the layers shown in FIG. 3A to create welded areas 7 that bind the layers together and form the composite of the invention.
Figure 3C:
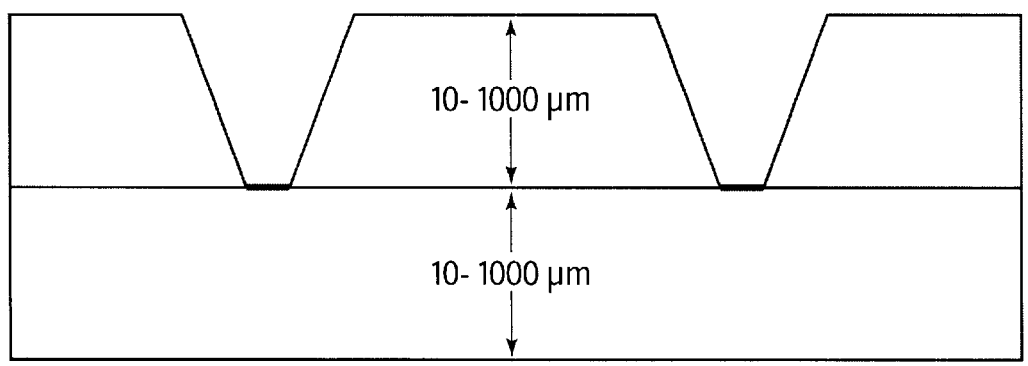
FIG. 3C shows, schematically, an embodiment of the invention having two layers that were spotwelded using a spotwelding tool like that depicted in FIGS. 1 and 2, wherein the thickness of each layer of the composite is between 10 and 1000 $\mu$m.

The bioactive glass fabric and the P(L/D)LA film (sizes 25×25 mm) were combined together using the spot welding method according to this invention. The surface of the welding head had round welding spots of diameter of 1.5 mm and the distance between adjacent spots was 3 mm. FIG. 2 shows schematically the geometry of the welding tool surface. The layers were located between the welding head (upper tool) and the smooth plate (lower tool) of an ultrasonic welding equipment (model Rinco MP-201, PCS II, available from Rinco Ultrasonics AG, Romaushom, Switzerland). The ultrasonic welding time used was between 0.1–0.5 s and the welding pressure was between 0.8–1.5 MPa. The final composite had a stiff, but ductile structure and thickness of 0.8 mm. The samples were sterilized with γ-irradiation.

EXAMPLE 3

A comparison of bone growth to repair a 15×15×10 mm defect in a sheep's tibia was carried out by using each of the following three methods on the defect:

A. The defect was left uncovered.

B. The defect was filled with crushed bioactive glass (composition: $Na_2O$ 6 wt-%, $K_2O$ 12 wt-%, MgO 5 wt-%, CaO 20 wt-%, $P_2O_5$ 4 wt-% and $SiO_2$ 53 wt-%) with nominal particle size 200 μm and left uncovered.

C. The defect was filled with crushed bioactive glass (the same glass as above in method B) with nominal particle size 200 μm, and the defect was covered with a composite device prepared as described in Example 2. The implant device was fixed by locating the bioactive glass fiber side towards the bone and attaching the implant over the defect with four mini screws (diameter of 2.0 mm, length of 6.0 mm) made of the same copolymer as the copolymer used to make the film in the implant.

Each procedure was performed in triplicate, and the animals were sacrificed after 24 weeks in all cases.

In the case of series A the defect site showed only minimal healing with partial filling of connective tissue with no new bone formation. In the animals of series B, the gaps between bioactive glass particles in the defect were filled with new bone and fibrous tissue, but new bone did not grow up to the level of the intact bone surface. In the animals of series C, which corresponds to the invention, the defects were filled with new bone and connective tissue. The crushed bioactive glass particles were still present, but new bone and connective tissue formation was spread from the edges of the defect to the middle of it and new bone also existed under the implant covering the defect.

EXAMPLE 4

The bending stiffness of a device made according to this invention is compared to the stiffnesses of the specimens made with previously known methods.

Devices were made from a copolymer of L and DL lactic acid having a monomer ratio of 70/30 (i.v.=6 dl/g, available from Boehringer Ingelheim, Germany) and a copolymer of L and D lactic acid having a monomer ratio of 96/4 ( i.v.=6.8 dl/g, available from Purac biochem b.v., The Netherlands). The 70/30 copolymer was compression molded into the form of a sheet (film) having dimensions 10×40×1 mm. The 96/4 copolymer was melt spun as in Example 1. The filaments were knitted by using a weft-knitting machine, the fabric having loop size ca. 1 mm.

Device 1 was made by joining the above mentioned sheet (film) and fabric together by using a spot welding method according to this invention. The surface of the welding tool had diamond shaped welding spots. The size of the welding spots was 1×1 mm and the distance between adjacent spots was 5 mm. The above layers were combined between the welding tool and the smooth plate by compression molding using a compression pressure between 2–20 MPa and keeping the temperature of the welding tool between 60° C.–120° C. During the welding, the parts of the polymeric fabric under the welding spots were pressed into the polymeric sheet (film), but the fabric between the welding spots remained loose.

To compare the bending stiffness of Device 1, three different specimen types were manufactured according to known methods. Device 2 was manufactured by combining the above mentioned sheet and fabric between two smooth plates (no welding spots or points) under heat (100° C.) and compression (8 MPa), causing the fabric to be pressed completely into the sheet. Device 3 was plain PLDLA 70/30 sheet manufactured as described above. Device 4 was plain PLDLA 70/30 sheet manufactured as described above, which was further subjected to a thermal treatment for 5 minutes at 80° C. followed by rapid quenching.

The 3-point bending tests made according to a standard ASTM D790M-93 showed the following:

| Specimen type | Bending strength (MPa) | Bending strength (GPa) |
|---|---|---|
| Device 1 | 33.4 | 0.78 |
| Device 2 | 58.4 | 1.37 |
| Device 3 | 67.6 | 1.95 |
| Device 4 | 93.3 | 2.85 |

Device 1, which was made according to the invention, did not break in the bending strength test, but slipped out of the supporting noses of the bending tool at a bending force corresponding to the given bending strength of 33.4 MPa. The other Devices 2–4 expressed extensive cracking and/or broke completely in the bending test.

Thus, this example demonstrates that the devices of the invention are flexible and tough in comparison to prior art devices.

We claim:

1. A bioabsorbable two-dimensional surgical laminate composite having a total area and comprising at least two layers, wherein the layers are partially welded together by spot welding, wherein said spot welding produces a welded area in the layers that is between 1 and 40 percent of the total area of the composite.

2. A bioabsorbable two-dimensional composite according to claim 1, wherein at least one of the layers contains pores.

3. A bioabsorbable two-dimensional composite according to claim 2, wherein the size of the pores is between 30–2000 μm.

4. A bioabsorbable two-dimensional composite according to claim 1, wherein at least one of the layers is a continuous film layer.

5. A bioabsorbable two-dimensional composite according to claim 1, wherein at least one of the layers is made of a bioabsorbable polymer.

6. A bioabsorbable two-dimensional composite according to claim 5, wherein at least one of the layers is made of inorganic biomaterial fibers.

7. A bioabsorbable two-dimensional composite according to claim 6, wherein the thickness of each layer is between 10–1000 μm.

8. A bioabsorbable two-dimensional composite according to claim 7, wherein at least one of the layers includes at least one bioactive additive selected from the group consisting of inorganic particle fillers, drugs, growth factors, proteins or peptides.

9. A bioabsorbable two-dimensional composite according to claim 7, wherein at least one of the layers includes cultured cells.

10. A method of manufacturing a bioabsorbable 2-dimensional composite having a total area and at least two layers, comprising the steps of: applying a first layer over a second layer and spot welding said first layer at least partially to said second layer through the application of heat or pressure to said first or said second layer, wherein said spot welding produces a welded area in said first layer and said second layer that is between 1 and 40 percent of the total area of the composite.

* * * * *